United States Patent [19]

Geszler

[11] Patent Number: 5,738,220
[45] Date of Patent: Apr. 14, 1998

[54] DISTAL TIP PROTECTOR CAP

[75] Inventor: David M. Geszler, Moorpark, Calif.

[73] Assignee: Pacesetter, Inc., Sylmar, Calif.

[21] Appl. No.: 723,735

[22] Filed: Sep. 30, 1996

[51] Int. Cl.⁶ .................................................. B65D 85/00
[52] U.S. Cl. ........................... 206/726; 206/365; 604/192; 604/263
[58] Field of Search ........................ 206/363, 364, 206/365, 701, 722, 726; 607/126; 604/192, 263

[56] References Cited

U.S. PATENT DOCUMENTS

| | | | |
|---|---|---|---|
| 3,719,190 | 3/1973 | Avery | 128/418 |
| 4,262,678 | 4/1981 | Stokes | 128/786 |
| 4,623,336 | 11/1986 | Pedicano et al. | 604/192 |
| 4,688,560 | 8/1987 | Schultz | 128/92 YE |
| 4,892,525 | 1/1990 | Hermann, Jr. et al. | 604/263 |
| 4,954,105 | 9/1990 | Fischer | 439/864 |
| 4,986,817 | 1/1991 | Code | 604/192 |
| 5,078,692 | 1/1992 | Cuprak | 604/192 |
| 5,078,694 | 1/1992 | Wallace | 604/192 |
| 5,117,978 | 6/1992 | Blumenfeld et al. | 206/365 |
| 5,261,417 | 11/1993 | Osypka | 607/127 |
| 5,279,578 | 1/1994 | Cooke | 604/192 |
| 5,328,474 | 7/1994 | Raines | 604/263 |
| 5,347,078 | 9/1994 | Eckels | 206/365 |
| 5,423,881 | 6/1995 | Breyen et al. | 607/122 |
| 5,451,213 | 9/1995 | Teicher et al. | 604/192 |
| 5,505,705 | 4/1996 | Galpin et al. | 604/263 |
| 5,514,172 | 5/1996 | Mueller | 607/122 |
| 5,535,745 | 7/1996 | Ingram et al. | 128/642 |

*Primary Examiner*—David T. Fidei

[57] ABSTRACT

A protective device includes a cap member extending between a nose end having a chamber therein for freely receiving the distal electrode of an implantable medical lead having a plurality of outward angularly extending tines and a tail end and an integral conical shield defining a cavity at least partially protectively enveloping the tines. Retention members releasably attach the cap member to the distal electrode so as to inhibit its unintended removal and include a plurality of resilient elongated fingers of a silicone elastomer at the tail end equal in number to the tines at circumferentially spaced locations about a longitudinal axis of the device. Each adjacent pair of fingers is constructed so as the snappingly receive and capture the tine in engagement therewith such that removal of the tine from the retention recess by movement of the cap member in the opposite direction is positively inhibited by the transverse edges.

32 Claims, 3 Drawing Sheets

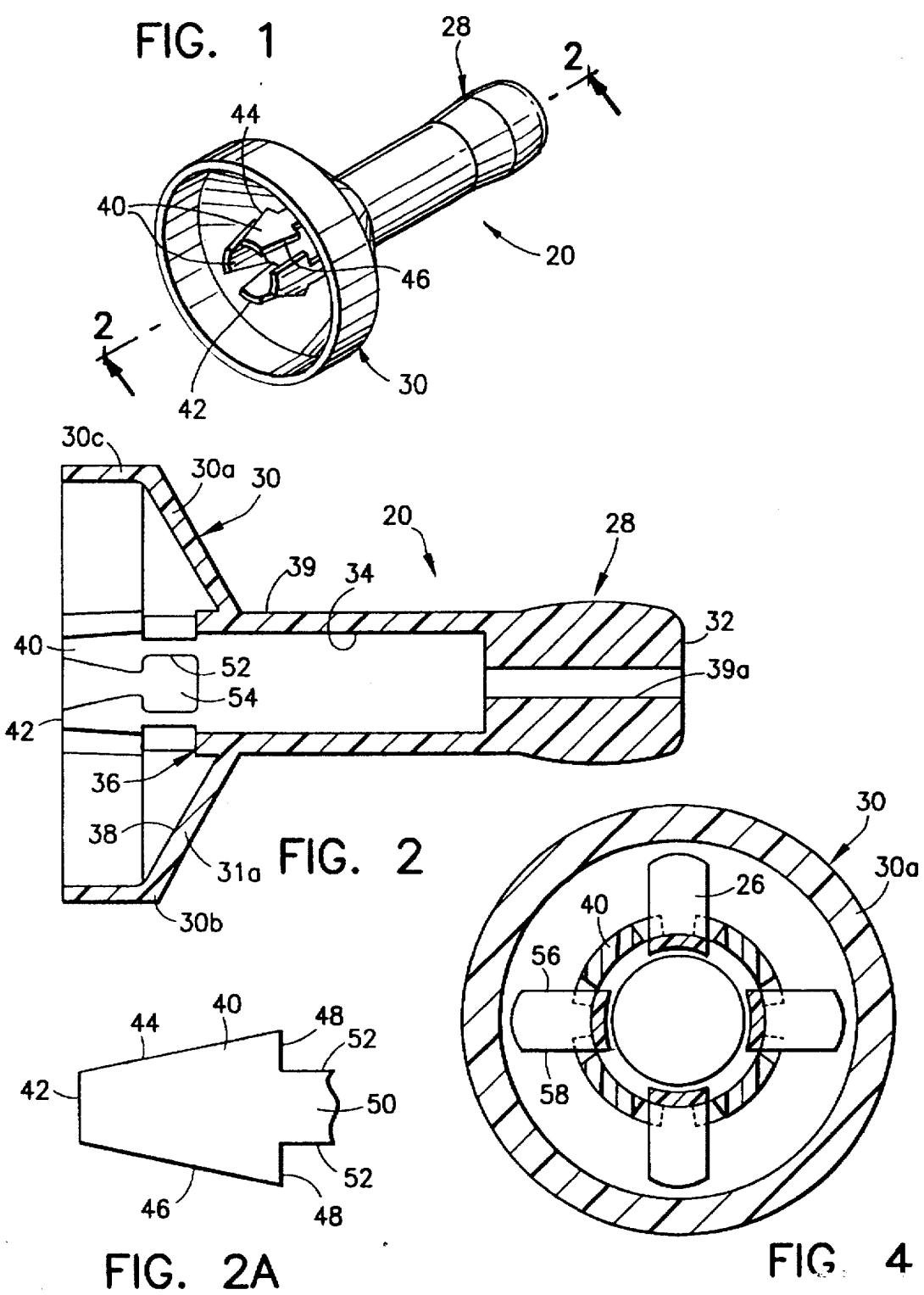

DISTAL TIP PROTECTOR CAP

FIELD OF THE INVENTION

This invention relates generally to a device for protecting the distal lead of an implantable medical device from damage during shipment and, more particularly, to such a device which protects both the distal electrode against abrasion and the like and the fixation tines against distortion.

This invention will be described in connection with its use for protecting the distal terminal end of an implantable pacemaker lead. However, it will be apparent to those skilled in the art that the invention has broader applicability to electrical terminals generally, irrespective of the particular medical device to which the lead is connected.

BACKGROUND OF THE INVENTION

It has been a known practice to package the distal leads of implantable medical devices such as pacemakers, defibrillators, and the like in plastic packages which are suitable for sterilizing such as with gas or autoclaving. For ease of description, but not intending to be limiting of the invention, discussion herein will relate to pacing leads. The pacing lead in the past has been inserted into the package appropriate to protect the distal electrode from scratching, abrading, and the like and has laid flat within the package during transportation, storage, and sterilizing prior to implantation in an individual. While this has been satisfactory for earlier designs of pacing leads, with the advent of new tined pacing leads, the tines have displayed amounts of nonconformity after being transported, stored, and sterilized. Such deformation is less than satisfactory from a medical point of view.

Pacing leads with tines have exhibited a certain amount of creep and deformation of the tines resulting in a change of the physical characteristics of the pacing lead.

One prior art practice has been to insert a ring-tip electrode having outwardly angular extending tines into the hole of a rectangular rubber member. This type of tine protector somewhat accomplished the end result of preventing creep and deformation of the tines but was less than one hundred percent satisfactory.

Typical of prior art in another field in which protection is sought for the end of an elongated member are the following U.S. patents which disclose protective devices for the needles of hypodermic syringes and the like:

| U.S. Pat. No. | Inventor(s) | Issued |
|---|---|---|
| 5,279,578 | Cooke | 01/18/94 |
| 5,078,694 | Wallace | 01/07/92 |
| 5,078,692 | Cuprak | 01/07/92 |
| 4,986,817 | Code | 01/22/91 |
| 4,892,525 | Hermann, Jr. et al. | 01/09/90 |
| 4,623,336 | Pedicano et al. | 11/18/86 |

U.S. Pat. No. 4,262,678 issued Apr. 21, 1981 to Stokes discloses a pacing lead with a tine protector. According to one embodiment of that invention, the tine protector includes a block shaped housing having four sides and a bottom, a first round hole located in one of the sides, a vertical longitudinal slit, and a second round hole geometrically located in the opposing side whereby the first hole accommodates the electrode and the second hole accommodates the lead of the pacing lead thereby enclosing the tines spaced about the electrode within the five-sided enclosure.

It was in light of the foregoing that the present invention was conceived and is now hereby reduced to practice. The present invention overcomes the disadvantages of the prior art problems by providing protection for a distal electrode as well as a tine protector for more improved protection of the tines spaced about an electrode of a pacing lead while providing yet additional benefits and advantages.

SUMMARY OF THE INVENTION

The present invention relates to a protective device which includes a cap member extending between a nose end and a tail end. The nose end has a chamber therein for freely receiving the distal electrode of an implantable medical lead having a plurality of outward angularly extending tines and an integral conical shield defining a cavity at least partially protectively enveloping the tines. Retention members releasably attach the cap member to the distal electrode so as to inhibit its unintended removal and include a plurality of resilient elongated fingers of a silicone elastomer at the tail end equal in number to the tines at circumferentially spaced locations about a longitudinal axis of the device. The fingers are parallel with the longitudinal axis, extend in a direction away from the nose end to an extremity, and have opposed lateral cam edges which increase in width with increasing distance away from the extremity until opposed transverse edges are reached. Each adjacent pair of fingers defines cooperatively positioned opposed retention recesses, one recess adjacent each of the transverse edges such that as the cap member is advanced in the direction of the distal electrode for mounting attachment thereto, the opposed lateral cam edges engage opposed edges of an intermediate associated tine until the associated transverse edges are reached whereupon the retention recess snappingly receives and captures the tine in engagement therewith such that removal of the tine from the retention recess by movement of the cap member in the opposite direction is inhibited by the transverse edges.

The protector cap of the invention is a silicone molded part intended to protect the tip of the pacer lead from damage during shipping while in the sterile package. The currently used protector cap, generally similar to the construction disclosed in the Stokes U.S. Pat. No. 4,262,678, noted above, is inadequate because of its large mass and high profile and because, statistically, it fails to remain protectively engaged on the tined tip of the lead, during shipping. UPS (United Parcel Service) shipping tests have proved the new protector cap to be superior in design, for retention characteristics. The new cap of the invention is cosmetically more appealing in size and shape because of its low profile configuration. It would also be less costly to produce by utilizing a liquid silicone molding process using bio medical materials.

The silicone distal protector cap of the invention is a molded shroud including a plurality of resilient elongated fingers composed of a medical grade silicone elastomer having a hardness in the range of approximately 50–90 durometers. The shroud covers and protects the distal electrode tip surfaces. It also protects the molded tine configuration from distortion. The structure of the protector cap is such as to allow for easy insertion of the root of the tines, four in number, to engage with the inside retention recesses, four in number, of the cap. Reverse movement or attempted removal of the cap causes an increase in retention forces, because of the retention recess configuration. Complete removal of the cap is accomplished by the ability of the molded silicone section too yield without affecting the tine configuration. Both the design of the retention recess and the hardness of the silicone play an important part in the configuration of the protector cap of the invention. After extensive bio-testing, it has been determined that silicone elastomer is a qualified medical grade material.

Accordingly, a primary object of the present invention is to provide a device for protecting the distal lead of an implantable medical device from damage prior to its use.

Another object of the present invention is to provide such a device which protects both the distal electrode against abrasion and the like and the fixation tines against distortion.

A further object of the present invention is to provide a protective device for the distal electrode of an implantable medical lead having a plurality of outward angularly extending tines comprising a first guard member for protecting the distal electrode, a second guard member for protecting the tines, and a retention member for releasably attaching the first and second guard members to the distal electrode so as to inhibit unintended removal of the first and second guard members from the distal electrode.

Still another object of the invention is to provide such a device wherein the first guard member includes a cap member extending between a nose end having a chamber therein for freely receiving the distal electrode therein and a tail end distant from said nose end and wherein the second guard means includes a conical shield integral with the cap member defining a cavity at least partially enveloping the tines for their protection.

Yet a further object of the present invention is to provide such a device wherein the retention members include a plurality of resilient elongated fingers equal in number to the number of the tines of the medical lead at circumferentially spaced locations about the longitudinal axis at the tail end, each of the fingers being generally parallel with the longitudinal axis, extending in a direction away from said nose end to an extremity, and increasing in width with increasing distance away from the extremity as defined by opposed lateral cam edges until opposed transverse edges are reached, an integral base element having opposed base edges connecting each of the fingers to the tail end and defining a pair of opposed retention recesses, one retention recess adjacent each of the transverse edges such that as the cap member is advanced in the direction of the distal electrode in axial alignment therewith for mounting attachment thereto, the opposed lateral cam edges of each adjacent pair of the fingers engage opposed edges of an intermediate associated one of the tines of the medical lead until the associated transverse edges are reached whereupon the retention recess snappingly receives and captures the tine in engagement therewith such that removal of the tine from the retention recess by movement of the cap member in the opposite direction is inhibited by the transverse edges.

Yet another object of the invention is to provide such a device wherein the resilient elongated fingers are composed of a silicone elastomer.

Yet a further object of the invention is to provide such a device wherein the resilient elongated fingers are composed of a medical grade silicone elastomer having a hardness the range of approximately 50–90 durometers.

Still a further object of the invention is to provide such a device wherein the cap member has a vent hole extending between the nose end and the chamber to allow entry to the tip electrode of a suitable sterilization gas for proper sterilization after being packaged.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

FIG. 1 is a perspective view of a protective device embodying the present invention;

FIG. 2 is a cross-section view of the protective device of the invention taken generally along line 2—2 in FIG. 2.

FIG. 2A is a detail side elevation view of a retention component of the protective device of the invention;

FIG. 4 is a cross-section view side elevation view taken generally along line 4—4 in FIG. 3C;

DETAILED DESCRIPTION OF THE PREFERRED EMBODIMENT

Figure 3A:
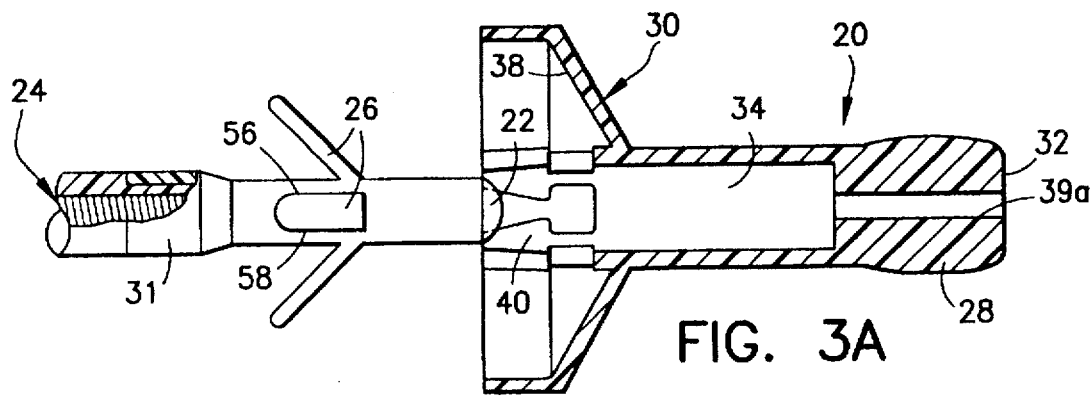
FIGS. 3A, 3B, and 3C are cross-section views, respectively, of the protective device of FIG. 1, similar to FIG. 2, illustrating three successive positions of a distal lead being inserted into mounting attachment with the protective device.

Turn now to the drawings and, initially, to FIGS. 1 and 2 which generally illustrate a protective device 20 for the distal electrode 22 of an implantable medical lead 24 having a plurality of outward angularly extending tines 26 (FIG. 3A). Typically, the distal electrode 22 is formed with a TiN coating. The protective device 20 includes a first guard, or cap, member 28 for protecting the distal electrode 22 and a second guard member, or shield, 30 for protecting the tines 26. The tines 26 are an integral part of a sleeve 31 of suitable plastic material, typically silicone, fittingly applied to, and overlying, the medical lead 24.

The cap member 28 extends between a nose end 32 having a chamber 34 therein for freely receiving the distal electrode therein (see FIGS. 3A–3C) and a tail end 36 distant from the nose end. The shield 30 is integral with the cap member and defines a cavity 38 at least partially enveloping the tines 26 for their protection (see FIGS. 3C and 5). The shield 30 includes a conical shield member 30a (FIG. 2) extending radially outwardly from the outer peripheral surface 39 of the cap member 28 intermediate the nose end 32 and the tail end 36 and away from the nose end with increasing distance away from the outer peripheral surface 39 to an outermost rim 30b. An annular shield member 30c is integral with the conical shield member 30a and extends from the outermost rim 30b in a direction away from the nose end 32. The cap member 28 also desirably has a vent hole 39a extending between the nose end 32 and the chamber 34 for sterilization of the distal electrode 22 while still in its protective packaging.

The protective device 20 also includes retention members in the form of a plurality of resilient elongated fingers 40 which are equal in number to the number of the tines 26 of the medical lead 24. The fingers 40 operate for releasably attaching the cap member 28 and the shield 30 to the distal electrode 22 so as to inhibit unintended removal of the cap member and shield from the distal electrode 22.

The fingers 40 are located at circumferentially spaced locations about the longitudinal axis of the protective device 20 at the tail end 36. Each of the fingers is generally parallel with the longitudinal axis of the protective device 20, extends in a direction away from the nose end 32 to an extremity 42 (FIG. 2A), and increases in width with increasing distance away from the extremity 42, as defined by opposed lateral cam edges 44, 46 until opposed transverse edges 48 are reached. An integral base element 50 having opposed base edges 52 connects each of the fingers 40 to the tail end 36. The base edges 52 and transverse edges of adjacent fingers 40 define a retention recess 54 (FIG. 2). The transverse distance between the base edges 52 of the base elements 50 of adjacent fingers 40 is no less than the width of the tine 26 of a lead 24 captured between them.

For purposes of the invention, the resilient elongated fingers 40 are desirably composed of a medical grade silicone elastomer having a hardness in the range of approximately 50-90 durometers and preferably in the range of 60-70 durometers.

With this construction, as the cap member 28 is advanced in the direction of the distal electrode 22 while in axial alignment therewith for mounting attachment to the distal electrode, viewing FIGS. 3A, 3B, 3C and 6A, 6B, 6C, the opposed lateral cam edges 44, 46 of each adjacent pair of the fingers 40 engage opposed edges 56, 58 (FIG. 2) of an intermediate associated one of the tines 26 of the medical lead 24. The protective cap 20 may be rotated about its longitudinal axis in the manner indicated by arrows 60 in FIG. 6B to assure engagement of the cam edges 44, 46 with the opposed edges 56, 58. Advancement continues until the associated transverse edges 48 (FIG. 2A) are reached whereupon the retention recess 54 snappingly receives and captures the tins 26 in engagement therewith. When this operation has been accomplished, removal of the tins from the retention recess 54 by movement of the cap member 28 in the opposite direction is inhibited by the transverse edges 48.

The resilience of the fingers 40 is such that intended removal of the protective device 20 from the medical lead 24 can be readily achieved while unintended removal is substantially inhibited.

Figure 3B:
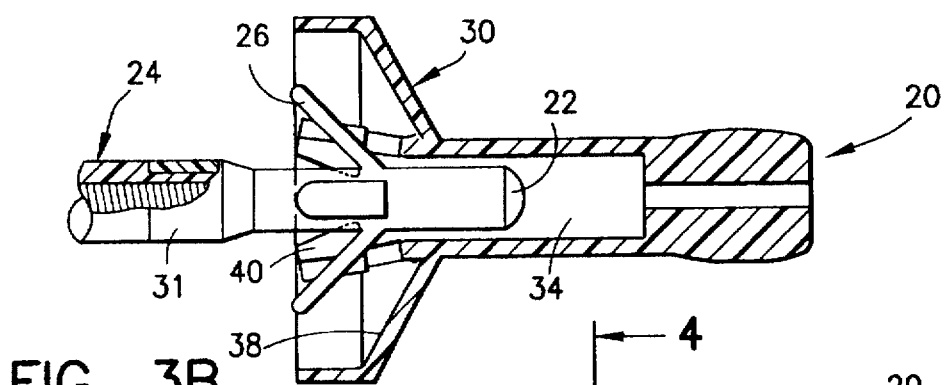
Figure 3C:
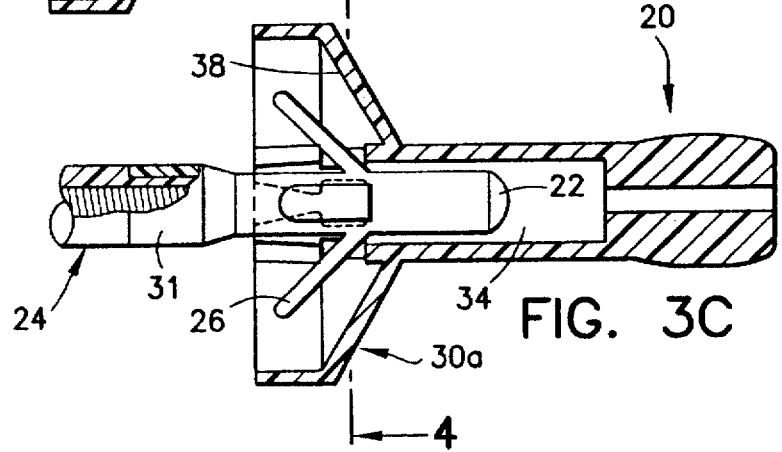
Figure 5:
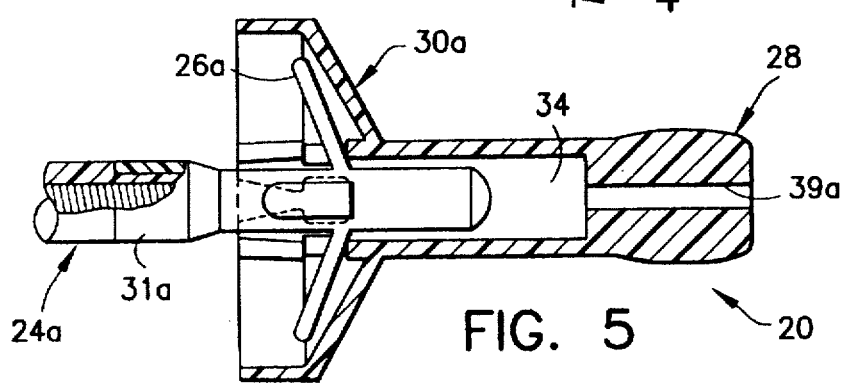
FIG. 5 is a cross-section view, similar to FIG. 3C, illustrating the protector cap of the invention applied to another embodiment of distal lead.
Figure 6A:
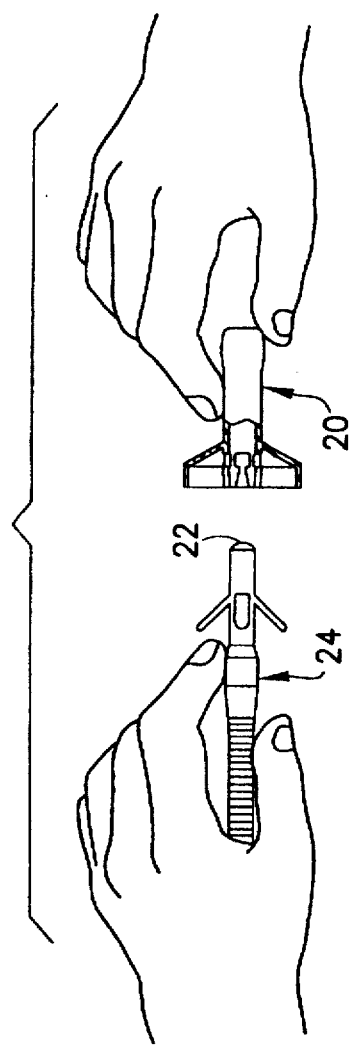
FIGS. 6A, 6B, and 6C are side elevation views, respectively, illustrating three successive positions during the manual insertion of a distal lead tip into the mounting attachment of the protective device.
Figure 6B:
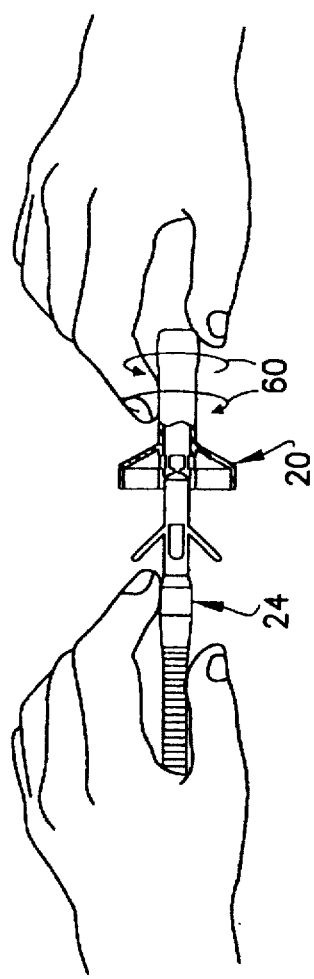
Figure 6C:
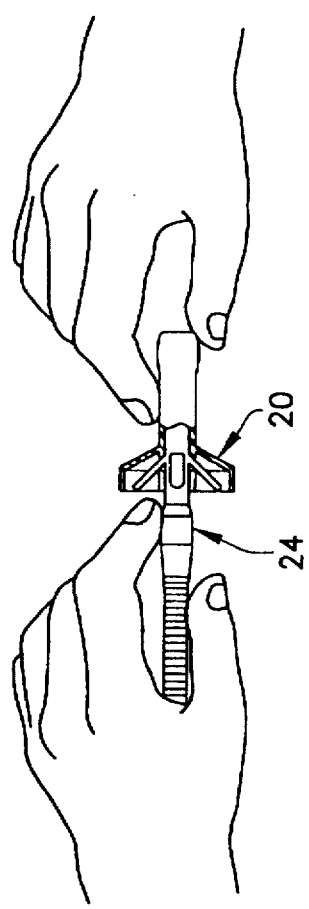

As will be clear from viewing FIG. 5, the protective device 20 is capable of providing the desired protection for a lead 24a whose tines 26a of sleeve e exhibit a sweepback of 30°, for example, as compared to the sweepback of 45° illustrated for the lead 24 in FIGS. 3A-3C. These particular values of sweepback are not intended to be controlling but only illustrative of the broad range of configurations of leads to which the invention is applicable.

In recapitulation, the protective device 20 of the invention is cosmetically appealing both on the medical lead 24 and in the sterile package (not shown) in which the medical lead is provided prior to use. It offers improved protection of the lead distal region over known devices, particularly the TiN coated electrode tip. The protective device 20 may be easily installed on a lead and is designed so as to automatically position itself on the medical lead when properly inserted. Also, the protective device 20 is readily removable by medical personnel and readily disposable, subsequently.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A protective device for the distal electrode of an implantable medical lead having a plurality of outward angularly extending tines comprising:

a cap member extending between a nose end having a chamber for freely receiving therein the distal electrode of the medical lead and a tail end distant from said nose end; and retention means at said tail end for releasably positively gripping the tines of the medical lead preventing relative rotation between said cap member and the distal electrode and inhibiting unintended removal of said cap member from the distal electrode.

2. A protective device, as set forth in claim 1, including shield means integral with said cap member extending radially outwardly therefrom and defining a cavity partially enveloping the tines of the medical lead for protection thereof.

3. A protective device, as set forth in claim 1, wherein said cap member has an outer peripheral surface; and wherein said shield means includes:

a conical shield member extending radially outwardly from said outer peripheral surface intermediate said nose end and said tail end and away from said nose end with increasing distance away from said outer peripheral surface to an outermost rim; and an annular shield member integral with said conical shield and extending from said outermost rim in a direction away from said nose end.

4. A protective device, as set forth in claim 3, wherein said annular shield member extends to a circular edge which lies in a plane generally perpendicular to the longitudinal axis of said cap member and containing said extremities of said fingers.

5. A protective device, as set forth in claim 1:

wherein said cap member is generally cylindrical and has a longitudinal axis; and wherein said retention means includes a plurality of resilient elongated fingers equal in number to the number of the tines of the medical lead at circumferentially spaced locations about the longitudinal axis at said tail end, each of said fingers being generally parallel with the longitudinal axis, extending in a direction away from said nose end to an extremity, and increasing in width with increasing distance away from said extremity as defined by opposed lateral cam edges until opposed transverse edges are reached, an integral base element having opposed base edges connecting each of said fingers to said tail end, said base edges and said transverse edges of an adjacent pair of said fingers defining a retention recess such that as said cap member is advanced in the direction of the distal electrode in axial alignment therewith for mounting attachment thereto, said opposed lateral cam edges of each adjacent pair of said fingers engage opposed edges of an intermediate associated tine of the medical lead until said associated transverse edges are reached whereupon the retention recess snappingly receives and captures the tine in engagement therewith such that removal of the tine from the retention recess by movement of said cap member in the opposite direction is inhibited by said transverse edges.

6. A protective device, as set forth in claim 5, wherein the transverse distance between said base edges of said base elements of adjacent ones of said fingers is no less than the width of the tine of a lead captured therebetween.

7. A protective device, as set forth in claim 5, wherein said resilient elongated fingers are composed of a silicone elastomer.

8. A protective device, as set forth in claim 5, wherein said resilient elongated fingers are composed of a medical grade silicone elastomer having a hardness in the range of approximately 50–90 durometers.

9. A protective device, as set forth in claim 1, wherein said cap member has a vent hole extending between said nose end and the chamber.

10. In combination:
   an implantable medical lead including a distal electrode and a plurality of outward angularly extending tines; and
   a protective device for said distal electrode and said tines including:
      a cap member extending between a nose end having a chamber therein for freely receiving said distal electrode therein and a tail end distant from said nose end; and
      retention means for releasably gripping said tines so as to inhibit unintended removal of said cap member from said distal electrode.

11. A combination, as set forth in claim 10, including shield means integral with said cap member extending radially outwardly therefrom and defining a cavity partially enveloping said tines of said medical lead for protection thereof.

12. A combination, as set forth in claim 10, wherein said cap member has an outer peripheral surface; and
wherein said shield means includes:
   a conical shield member extending radially outwardly from said outer peripheral surface intermediate said nose end and said tail end and away from said nose end with increasing distance away from said outer peripheral surface to an outermost rim; and
   an annular shield member integral with said conical shield and extending from said outermost rim in a direction away from said nose end.

13. A combination, as set forth in claim 12, wherein said annular shield member extends to a circular edge which lies in a plane generally perpendicular to the longitudinal axis of said cap member and generally containing said extremities of said fingers.

14. A combination, as set forth in claim 10, wherein said retention means includes a plurality of resilient elongated fingers equal in number to the number of said tines of said medical lead at circumferentially spaced locations about the longitudinal axis at said tail end, each of said fingers being generally parallel with the longitudinal axis, extending in a direction away from said nose end to an extremity, and increasing in width with increasing distance away from said extremity as defined by opposed lateral cam edges until opposed transverse edges are reached, an integral base element having opposed base edges connecting each of said fingers to said tail end, said base edges and said transverse edges of an adjacent pair of said fingers defining a retention recess such that as said cap member is advanced in the direction of said distal electrode in axial alignment therewith for mounting attachment thereto, said opposed lateral cam edges of each adjacent pair of said fingers engage opposed edges of an intermediate associated one of said tines of said medical lead until said associated transverse edges are reached whereupon the retention recess snappingly receives and captures said tine in engagement therewith such that removal of said tine from the retention recess by movement of said cap member in the opposite direction is inhibited by said transverse edges.

15. A combination, as set forth in claim 11, wherein the transverse distance between said base edges of said base elements of adjacent ones of said fingers is no less than the width of said associated tine of said medical lead captured therebetween.

16. A combination, as set forth in claim 11, wherein said resilient elongated fingers are composed of a silicone elastomer.

17. A combination, as set forth in claim 11, wherein said resilient elongated fingers are composed of a medical grade silicone elastomer having a hardness in the range of approximately 50–90 durometers.

18. A combination, as set forth in claim 10, wherein said cap member has a vent hole extending between said nose end and the chamber.

19. In combination:
   an implantable medical lead including a distal electrode and a plurality of outward angularly extending tines;
   first guard means for protecting said distal electrode;
   second guard means for protecting said tines; and
   retention means for releasably attaching said first and second guard means to said distal electrode so as to inhibit unintended removal of said first and second guard means from said distal electrode.

20. A combination, as set forth in claim 19, wherein said first guard means includes a cap member extending between a nose end having a chamber therein for freely receiving said distal electrode therein and a tail end distant from said nose end; and
   wherein said second guard means includes a conical shield integral with said cap member defining a cavity at least partially enveloping said tines for protection thereof.

21. A combination, as set forth in claim 19, wherein said retention means includes a plurality of resilient elongated fingers equal in number to the number of said tines of said medical lead at circumferentially spaced locations about the longitudinal axis at said tail end, each of said fingers being generally parallel with the longitudinal axis, extending in a direction away from said nose end to an extremity, and increasing in width with increasing distance away from said extremity as defined by opposed lateral cam edges until opposed transverse edges are reached, an integral base element having opposed base edges connecting each of said fingers to said tail end, said base edges and said transverse edges of an adjacent pair of said fingers defining a retention recess such that as said cap member is advanced in the direction of said distal electrode in axial alignment therewith for mounting attachment thereto, said opposed lateral cam edges of each adjacent pair of said fingers engage opposed edges of an intermediate associated one of said tines of said medical lead until said associated transverse edges are reached whereupon the retention recess snappingly receives and captures said tine in engagement therewith such that removal of said tine from the retention recess by movement of said cap member in the opposite direction is inhibited by said transverse edges.

22. A combination, as set forth in claim 20, wherein the transverse distance between said base edges of said base elements of adjacent ones of said fingers is no less than the width of said tine of an associated said lead captured therebetween.

23. A combination, as set forth in claim 20, wherein said resilient elongated fingers are composed of a silicone elastomer.

24. A combination, as set forth in claim 20, wherein said resilient elongated fingers are composed of a medical grade silicone elastomer having a hardness in the range of approximately 50–90 durometers.

25. A combination, as set forth in claim 19, wherein said cap member has a vent hole extending between said nose end and the chamber.

26. A protective device for the distal electrode of an implantable medical lead having a plurality of outward angularly extending tines comprising:

first guard means for protecting the distal electrode;

second guard means for protecting the tines; and retention means for releasably attaching said first and second guard means to the distal electrode so as to inhibit unintended removal of said first and second guard means from the distal electrode while preventing relative rotation between said first and second guard means as a unit and the distal electrode as a unit.

27. A protective device, as set forth in claim 6, wherein said first guard means includes a cap member extending between a nose end having a chamber therein for freely receiving the distal electrode therein and a tail end distant from said nose end; and wherein said second guard means includes a conical shield integral with said cap member defining a cavity at least partially enveloping the tines for protection thereof.

28. A protective device, as set forth in claim 26, wherein said retention means includes a plurality of resilient elongated fingers equal in number to the number of the tines of the medical lead at circumferentially spaced locations about the longitudinal axis at said tail end, each of said fingers being generally parallel with the longitudinal axis, extending in a direction away from said nose end to an extremity, and increasing in width with increasing distance away from said extremity as defined by opposed lateral cam edges until opposed transverse edges are reached, an integral base element having opposed base edges connecting each of said fingers to said tail end, said base edges and said transverse edges of an adjacent pair of said fingers defining a retention recess such that as said cap member is advanced in the direction of the distal electrode in axial alignment therewith for mounting attachment thereto, said opposed lateral cam edges of each adjacent pair of said fingers engage opposed edges of an intermediate associated one of the tines of the medical lead until said associated transverse edges are reached whereupon the retention recess snappingly receives and captures the tine in engagement therewith such that removal of the tine from the retention recess by movement of said cap member in the opposite direction is inhibited by said transverse edges.

29. A protective device, as set forth in claim 28, wherein the transverse distance between said base edges of said base elements of adjacent ones of said fingers is no less than the width of the tine of a lead captured therebetween.

30. A protective device, as set forth in claim 28, wherein said resilient elongated fingers are composed of a silicone elastomer.

31. A protective device, as set forth in claim 28, wherein said resilient elongated fingers are composed of a medical grade silicone elastomer having a hardness in the range of approximately 50–90 durometers.

32. A protective device, as set forth in claim 26, wherein said cap member has a vent hole extending between said nose end and the chamber.

* * * * *